United States Patent
Demeulenaere et al.

(10) Patent No.: US 6,419,710 B1
(45) Date of Patent: Jul. 16, 2002

(54) COMPOSITION FOR THE OXIDATION DYEING OF KERATIN FIBERS AND DYEING PROCESS USING THIS COMPOSITION

(75) Inventors: Christelle Demeulenaere, Le Vesinet; Mireille Maubru, Chatou, both of (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/504,622

(22) Filed: Feb. 15, 2000

(30) Foreign Application Priority Data

Feb. 16, 1999 (FR) ............................................ 99 01869

(51) Int. Cl.$^7$ ................................................. A61K 7/13
(52) U.S. Cl. ........................ 8/405; 8/406; 8/407; 8/410; 8/411; 8/412; 8/563
(58) Field of Search ............................. 8/405, 406, 407, 8/410, 411, 412, 463

(56) References Cited

U.S. PATENT DOCUMENTS 6,241,784 B1 * 6/2001 De la Mettrie et al. ......... 8/406

FOREIGN PATENT DOCUMENTS

| DE | 2 359 399 | 6/1975 |
|----|-----------|--------|
| DE | 38 43 892 | 6/1990 |
| DE | 41 33 957 | 4/1993 |
| DE | 195 43 988 | 5/1997 |
| EP | 0 310 675 | 4/1989 |
| EP | 0 688 558 | 12/1995 |
| EP | 0 716 846 | 6/1996 |
| FR | 2 586 913 | 3/1987 |
| FR | 2 733 749 | 11/1996 |
| FR | 2 750 048 | 12/1997 |
| FR | 2 769 210 | 4/1999 |
| FR | 2 769 220 | 4/1999 |
| GB | 1 026 978 | 4/1966 |
| GB | 1 153 196 | 5/1969 |
| JP | 88-169571 | 7/1988 |
| JP | 9-110659 | 4/1997 |
| WO | WO 94/08969 | 4/1994 |
| WO | WO 94/08970 | 4/1994 |
| WO | WO 96/15765 | 5/1996 |
| WO | WO 97/19998 | 6/1997 |

OTHER PUBLICATIONS

English language Derwent Abstract of FR 2 769 210, Apr. 1999.
English language Derwent Abstract of FR 2 769 220, Apr. 1999.
English language Derwent Abstract of JP 9–110659, Apr. 1997.
English language Derwent Abstract of EP 0 688 558, Dec. 1995.
English language Derwent Abstract of DE 23 59 399, Jun. 1975.
English language Derwent Abstract of DE 3 843 892, Jun. 1990.
English language Derwent Abstract of DE 41 33 957, Apr. 1993.
English language Derwent Abstract of DE 195 43 988, May 1997.
English language abstract of FR 2 586 913, Mar. 1987.
English language abstract of FR 2 733 749, Nov. 1996.
English language Derwent Abstract of FR 2 750 048, Dec. 1997.

* cited by examiner

*Primary Examiner*—Yogendra N. Gupta
*Assistant Examiner*—Eisa Elhilo
(74) *Attorney, Agent, or Firm*—Finnegan, Henderson, Farabow, Garrett and Dunner, L.L.P.

(57) ABSTRACT

The invention relates to a ready-to-use composition for the oxidation dyeing of keratin fibers, especially human keratin fibers, such as the hair, having, in a medium suitable for dyeing, at least one oxidation base, at least one coupler chosen from substituted meta-diphenols, and at least one enzyme of 2-electron oxidoreductase type in the presence of at least one donor for the enzyme, with the composition being free from any additional coupler chosen from substituted meta-phenylenediamines; the invention also relates to the dyeing process using this composition.

43 Claims, No Drawings

COMPOSITION FOR THE OXIDATION DYEING OF KERATIN FIBERS AND DYEING PROCESS USING THIS COMPOSITION

The invention relates to a composition for the oxidation dyeing of keratin fibers, and, in particular, human keratin fibers, such as the hair, comprising, in a medium suitable for dyeing, at least one oxidation base, at least one coupler chosen from substituted meta-diphenols, and at least one enzyme of 2-electron oxidoreductase type in the presence of at least one donor for the enzyme, the composition being free from any additional coupler chosen from substituted meta-phenylenediamines. The invention also relates to the dyeing process using this composition.

It is known to dye keratin fibers, especially human hair, with dye compositions containing oxidation dye precursors, in particular, ortho- or para-phenylenediamines, ortho- or para-aminophenols and heterocyclic bases, generally referred to as oxidation bases. Oxidation dye precursors, or oxidation bases, are colorless or weakly colored compounds which, when combined with oxidizing products, can give rise to colored compounds and dyes by a process of oxidative condensation.

It is also known that the shades obtained with these oxidation bases can be varied by combining them with couplers or color modifiers, the latter being chosen, in particular, from aromatic meta-diamines, meta-aminophenols, meta-diphenols and certain heterocyclic compounds. The variety of molecules used as oxidation bases and couplers allows a wide range of colors to be obtained.

The so-called "permanent" coloration obtained by means of these oxidation dyes must, moreover, satisfy a certain number of requirements. Thus, it must have no toxicological drawbacks, it must be able to give shades of the desired intensity and it must be able to withstand external agents (light, bad weather, washing, permanent-waving, perspiration, and rubbing). The dyes must also be able to cover white hair and, lastly, they must be as unselective as possible, i.e., they must give the smallest possible color differences along the same length of keratin fiber, which may in fact be differently sensitized (i.e., damaged) between its tip and its root.

The oxidation dyeing of keratin fibers is generally carried out in alkaline medium, in the presence of hydrogen peroxide. However, the use of alkaline media in the presence of hydrogen peroxide has the drawback of causing appreciable degradation of the fibers, as well as considerable bleaching of the keratin fibers, which is not always desirable.

The oxidation dyeing of keratin fibers can also be carried out using oxidizing systems other than hydrogen peroxide, such as enzymatic systems. Thus, it has already been proposed to dye keratin fibers, in particular, in European patent application EP-A-0,310,675, incorporated herein by reference, with compositions comprising an oxidation base and optionally a coupler, in combination with enzymes such as pyranose oxidase, glucose oxidase or uricase, in the presence of a donor for the enzymes. Although they are used under conditions that do not result in a degradation of the keratin fibers, comparable to that caused by the dyes used in the presence of hydrogen peroxide, these dyeing processes nevertheless lead to colorations that are not entirely satisfactory, in particular, regarding their intensity, strength, and resistance to the various attacking factors to which hair may be subjected.

The inventors have now discovered that it is possible to obtain new dyes, which are capable of leading to intense colorations, without giving rise to any significant degradation of the keratin fibers, and which are relatively unselective and show good resistance to the various attacking factors to which hair may be subjected. These dyes may be obtained by combining at least one oxidation base, at least one coupler chosen from substituted meta-diphenols, and at least one enzyme of 2-electron oxidoreductase type in the presence of at least one donor for the enzyme, the composition being free from any additional coupler chosen from substituted meta-phenylenediamines. This discovery forms the basis of the present invention.

A first subject of the invention is thus a ready-to-use composition for the oxidation dyeing of keratin fibers, and, in particular, human keratin fibers such as the hair, characterized in that it comprises, in a medium which is suitable for dyeing:

at least one oxidation base,
at least one coupler chosen from substituted meta-diphenols,
at least one enzyme of 2-electron oxidoreductase type, and
at least one donor for the enzyme;

the composition being free from any additional coupler chosen from substituted meta-phenylenediamines and from any polymer chosen from anionic amphiphilic polymers comprising at least one hydrophilic unit and at least one allyl ether unit having a fatty chain. The ready-to-use dye composition according to the invention leads to intense, relatively unselective colorations with excellent properties of resistance both to atmospheric agents, such as light and bad weather, and to perspiration and the various treatments to which hair may be subjected, e.g., washing and permanent-waving. These properties are particularly noteworthy in regard to the intensity of the colorations obtained. A subject of the invention is also a process for the oxidation dyeing of keratin fibers using this ready-to-use dye composition.

The 2-electron oxidoreductase(s) used in the ready-to-use dye composition according to the invention can be chosen, in particular, from pyranose oxidases, glucose oxidases, glycerol oxidases, lactate oxidases, pyruvate oxidases and uricases. According to the invention, the 2-electron oxidoreductase is preferably chosen from uricases of animal, microbiological or biotechnological origin. Examples include uricase extracted from boar liver, uricase from *Arthrobacter globiformis*, as well as uricase from *Aspergillus flavus*. The 2-electron oxidoreductase(s) can be used in pure crystalline form or in a form diluted in a diluent, which is inert with respect to the 2-electron oxidoreductase. The 2-electron oxidoreductase(s) according to the invention preferably represent(s) from 0.01 to 20% by weight approximately relative to the total weight of the ready-to-use dye composition, and even more preferably from 0.1 to 5% by weight approximately relative to this weight.

According to the invention, the term "donor" is understood to refer to the various substrates involved in the functioning of the 2-electron oxidoreductase(s). The nature of the donor (or substrate) for the enzyme varies depending on the nature of the 2-electron oxidoreductase used. For example, as donors for the pyranose oxidases, mention may be made of D-glucose, L-sorbose and D-xylose; as a donor for the glucose oxidases, mention may be made of D-glucose; as donors for the glycerol oxidases, mention may be made of glycerol and dihydroxyacetone; as donors for the lactate oxidases, mention may be made of lactic acid and its salts; as donors for the pyruvate oxidases, mention may be made of pyruvic acid and its salts; and lastly, as donors for the uricases, mention may be made of uric acid and its salts.

The donor(s) (or substrate(s)) used according to the invention preferably represent(s) from 0.01 to 20% by weight approximately relative to the total weight of the ready-to-use dye composition in accordance with the invention, and even more preferably from 0.1 to 5% by approximately relative to this weight.

The nature of the oxidation base(s) used in the ready-to-use dye composition is not a critical factor. They can be chosen, in particular, from para-phenylenediamines, double bases, para-aminophenols, orthoaminophenols and heterocyclic oxidation bases.

Among the para-phenylenediamines that can be used as oxidation bases in the dye compositions in accordance with the invention, particular examples include the compounds of formula (I) below, and the acid addition salts thereof:

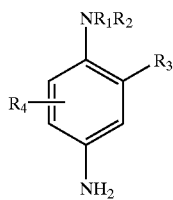

(I)

in which:
- $R_1$ represents a hydrogen atom, a $C_1$–$C_4$ alkyl radical, a $C_1$–$C_4$ monohydroxyalkyl radical, a $C_2$–$C_4$ polyhydroxyalkyl radical, a $(C_1$–$C_4)$alkoxy$(C_1$–$C_4)$alkyl radical, a $C_1$–$C_4$ alkyl radical substituted with a nitrogenous group, a phenyl radical or a 4'-aminophenyl radical;
- $R_2$ represents a hydrogen atom, a $C_1$–$C_4$ alkyl radical, a $C_1$–$C_4$ monohydroxyalkyl radical, a $C_2$–$C_4$ polyhydroxyalkyl radical, a $(C_1$–$C_4)$alkoxy$(C_1$–$C_4)$alkyl radical or a $C_1$–$C_4$ alkyl radical substituted with a nitrogenous group;
- $R_3$ represents a hydrogen atom, a halogen atom such as a chlorine, bromine, iodine or fluorine atom, a $C_1$–$C_4$ alkyl radical, a $C_1$–$C_4$ monohydroxyalkyl radical, a $C_1$–$C_4$ hydroxyalkoxy radical, an acetylamino($C_1$–$C_4$) alkoxy radical, a $C_1$–$C_4$ mesylaminoalkoxy radical or a carbamoylamino ($C_1$–$C_4$) alkoxy radical,
- $R_4$ represents a hydrogen or halogen atom or a $C_1$–$C_4$ alkyl radical.

Among the nitrogenous groups of formula (I) above, particular examples include amino, mono ($C_1$–$C_4$) alkylamino, di($C_1$–$C_4$)alkylamino, tri($C_1$–$C_4$)alkylamino, monohydroxy($C_1$–$C_4$)alkylamino, imidazolinium and ammonium radicals.

Among the para-phenylenediamines of formula (I) above, mention may be made more particularly of para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis (β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N-(β-methoxyethyl)-para-phenylenediamine, and the acid addition salts thereof.

Among the para-phenylenediamines of formula (I) above, para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis (β-hydroxyethyl)-para-phenylenediamine, 2-chloro-para-phenylenediamine and 2-β-acetylaminoethyloxy-para-phenylenediamine and the acid addition salts thereof are most particularly preferred.

According to the invention, the term double bases is understood to refer to the compounds containing at least two aromatic rings bearing amino and/or hydroxyl groups. Among the double bases which can be used as oxidation bases in the dye compositions according to the invention, particular examples include the compounds corresponding to formula (II) below, and the acid addition salts thereof:

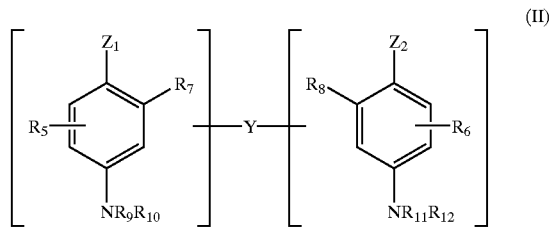

(II)

in which:
- $Z_1$ and $Z_2$, which may be identical or different, represent a hydroxyl or —$NH_2$ radical which may be substituted with a $C_1$–$C_4$ alkyl radical or with a linker arm Y;
- the linker arm Y represents a linear or branched alkylene chain containing from 1 to 14 carbon atoms, which may be interrupted by or terminated with one or more nitrogenous groups and/or one or more hetero atoms such as oxygen, sulphur or nitrogen atoms, and optionally substituted with one or more hydroxyl or $C_1$–$C_6$ alkoxy radicals;
- $R_5$ and $R_6$ represent a hydrogen or halogen -atom, a $C_1$–$C_4$ alkyl radical, a $C_1$–$C_4$ monohydroxyalkyl radical, a $C_2$–$C_4$ polyhydroxyalkyl radical, a $C_1$–$C_4$ aminoalkyl radical or a linker arm Y;
- $R_7$, $R_8$, $R_9$, $R_{10}$, $R_{11}$ and $R_{12}$, which may be identical or different, represent a hydrogen atom, a linker arm Y or a $C_1$–$C_4$ alkyl radical;

it being understood that the compounds of formula (II) contain only one linker arm Y per molecule.

Among the nitrogenous groups of formula (II) above, particular examples include amino, mono($C_1$–$C_4$) alkylamino, di($C_1$–$C_4$)alkylamino, tri($C_1$–$C_4$)alkylamino, monohydroxy($C_1$–$C_4$)alkylamino, imidazolinium and ammonium radicals.

Among the double bases of formula (II) above, mention may be made more particularly of N,N'-bis-(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis (4-aminophenyl)-tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the acid addition salts thereof.

Among these double bases of formula (II), N,N'-bis(β-hydroxyethyl)-N,N'-bis(4'-aminophenyl)-1,3-diaminopropanol and 1,8-bis(2,5-diaminophenoxy)-3,5-dioxaoctane, or one of the acid addition salts thereof, are particularly preferred.

Among the para-aminophenols that can be used as oxidation bases in the dye compositions according to the invention, particular examples include the compounds corresponding to formula (III) below, and the acid addition salts thereof:

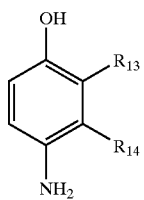

(III)

in which:

R$_{13}$ represents a hydrogen or halogen atom or a C$_1$–C$_4$ alkyl, C$_1$–C$_4$ monohydroxyalkyl, (C$_1$–C$_4$)alkoxy (C$_1$–C$_4$)alkyl, C$_1$–C$_4$ aminoalkyl or hydroxy (C$_1$–C$_4$) alkylamino (C$_1$–C$_4$) alkyl radical, R$_{14}$ represents a hydrogen or halogen atom or a C$_1$–C$_4$ alkyl, C$_1$–C$_4$ monohydroxyalkyl, C$_2$–C$_4$ polyhydroxyalkyl, C$_1$–C$_4$ aminoalkyl, C$_1$–C$_4$ cyanoalkyl or (C$_1$–C$_4$)alkoxy-(C$_1$–C$_4$)alkyl radical, it being understood that at least one of the radicals R$_{13}$ or R$_{14}$ represents a hydrogen atom.

Among the para-aminophenols of formula (III) above, mention may be made more particularly of para-aminophenol, 4-amino-3-methylphenol, 4-amino-3-fluorophenol, 4-amino-3-hydroxymethylphenol, 4-amino-2-methyl-phenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid addition salts thereof.

Among the ortho-aminophenols that can be used as oxidation bases in the dye compositions according to the invention, mention may be made more particularly of 2-aminophenol, 2-amino-5-methylphenol, 2-amino-6-methylphenol and 5-acetamido-2-aminophenol, and the acid addition salts thereof.

Among the heterocyclic bases that can be used as oxidation bases in the dye compositions according to the invention, mention may be made more particularly of pyridine derivatives, pyrimidine derivatives and pyrazole derivatives, and the acid addition salts thereof.

Among the pyridine derivatives, mention may be made more particularly of the compounds described, for example, in British patents GB 1,026,978 and GB 1,153,196, both incorporated herein by reference, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the acid addition salts thereof.

Among the pyrimidine derivatives, mention may be made more particularly of the compounds described, for example, in German patent DE 2,359,399, Japanese patents JP 88-169, 571 and JP 91-10659 or PCT patent application WO 96/15765, the disclosures of each of which are hereby incorporated by reference, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in French patent application FR-A-2 750 048, incorporated herein by reference, and among which mention may be made of pyrazolo{1,5-a}pyrimidine-3,7-diamine; 2,5-dimethylpyrazolo{1,5-a}pyrimidine-3,7-diamine; pyrazolo{5-a}pyrimidine-3,5-diamine; 2,7-dimethylpyrazolo{5-a}pyrimidine-3,5-diamine; 3-aminopyrazolo{1,5-a}pyrimidin-7-ol; 3-aminopyrazolo-{1,5-a}pyrimidin-5-ol; 2-(3-aminopyrazolo{1,5-a}-pyrimidin-7-ylamino)ethanol, 2-(7-aminopyrazolo{1,5-a}-pyrimidin-3-ylamino)ethanol, 2-{(3-aminopyrazolo{1,5-a}-pyrimidin-7-yl)-(2-hydroxyethyl)amino}ethanol, 2-{(7-aminopyrazolo{1,5-a}pyrimidin-3-yl)-(2-hydroxyethyl)-amino}ethanol, 5,6-dimethylpyrazolo{1,5-a}-pyrimidine-3,7-diamine, 2,6-dimethylpyrazolo{1,5-a}-pyrimidine-3,7-diamine, 2,5,N7, N7-tetramethylpyrazolo-{1,5-a}pyrimidine-3,7-diamine and 3-amino-5-methyl-7-imidazolylpropylamino-pyrazolo{1,5-a}pyrimidine, the tautomeric forms, when a tautomeric equilibrium exists, and the acid addition salts thereof.

Among the pyrazole derivatives, mention may be made more particularly of the compounds described in German patents DE 3,843,892, DE 4,133,957, PCT patent applications WO 94/08969, WO 94/08970, French patent application FR-A-2,733,749 and German patent application DE 195 43 988, the disclosures of each of which are incorporated herein by reference, such as 4,5-diamino-1-methylpyrazole, 3,4-diaminopyrazole, 4,5-diamino-1-(4'-chlorobenzyl)pyrazole, 4,5-diamino-1,3-dimethyl-pyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropyl-pyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-l-methylpyrazole, and the acid addition salts thereof.

The oxidation base(s) preferably represent(s) from 0.0005 to 12% by weight approximately relative to the total weight of the dye composition in accordance with the invention, and even more preferably from 0.005 to 8% by weight approximately relative to this weight.

The substituted meta-diphenol(s) that can be used as couplers in the ready-to-use dye composition according to the invention are preferably chosen from the compounds of formula (IV) below, and the acid addition salts thereof:

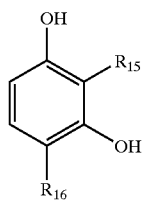

(IV)

in which:
R$_{15}$ and R$_{16}$, which may be identical or different, represent a hydrogen atom, a C$_1$–C$_4$ alkyl radical or a halogen atom chosen from chlorine, bromine and fluorine;

it being understood that at least one of the radicals R$_{15}$ and R$_{16}$ is other than a hydrogen atom.

Among the meta-diphenols of formula (IV) above, mention may be made more particularly of 2-methyl-1,3-dihydroxybenzene, 4-chloro-1,3-dihydroxy-benzene and 2-chloro-1,3-dihydroxybenzene, and the acid addition salts thereof. According to one particularly preferred embodiment of the invention, the dye composition contains 2-methyl-1,3-dihydroxybenzene and/or one of the acid addition salts thereof. The substituted meta-diphenol(s) that can be used as couplers preferably represent(s) from 0.0001 to 8% by weight approximately relative to the total weight of the dye composition, and even more preferably from 0.005 to 5% by weight approximately relative to this weight.

The dye composition according to the invention can also contain one or more additional couplers other than the substituted meta-aminophenols used according to the invention and other than the substituted meta-phenylenediamines that are excluded from the invention. Among these additional couplers, particular examples include resorcinol, meta-phenylenediamine, naphthols such as α-naphthol, meta-aminophenol, substituted meta-aminophenols such as, for example, 5-amino-2-methylphenol and 5-N-β-(hydroxyethyl)amino-2-methylphenol, and heterocyclic couplers such as, for example, 6-hydroxyindole, and the acid addition salts thereof. When they are used, the additional coupler(s) preferably represent(s) from 0.0001 to 8% by weight approximately relative to the total weight of the dye composition, and even more preferably from 0.005 to 0.5% by weight approximately relative to this weight.

The dye composition according to the invention can also contain one or more direct dyes, especially to modify the shades or to enrich them with glints.

In general, the acid addition salts that can be used in the context of the dye compositions of the invention (oxidation bases and couplers) are chosen, in particular, from the hydrochlorides, hydrobromides, sulphates, tartrates, lactates and acetates.

The medium suitable for dyeing (or support) for the ready-to-use dye composition according to the invention generally comprises water or a mixture of water and at least one organic solvent to dissolve the compounds that would not be sufficiently soluble in water. By way of organic solvents, mention may be made, for example, of C$_1$–C$_4$ alkanols, such as ethanol and isopropanol, glycerol, glycols and glycol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, similar products and mixtures thereof. The solvents can be present in proportions preferably ranging from 1 to 40% by weight approximately relative to the total weight of the dye composition, and even more preferably from 5 to 30% by weight approximately.

The pH of the ready-to-use composition in accordance with the invention is chosen such that the enzymatic activity of the 2-electron oxidoreductase is sufficient. It generally ranges from 5 to 11 approximately, and preferably from 6.5 to 10 approximately. It can be adjusted to the desired value using acidifying or basifying agents usually used for dyeing keratin fibers. Among the acidifying agents, examples include inorganic or organic acids such as hydrochloric acid, orthophosphoric acid, sulphuric acid, carboxylic acids such as acetic acid, tartaric acid, citric acid or lactic acid, and sulphonic acids.

Among the basifying agents, examples include aqueous ammonia, alkaline carbonates, alkanolamines such as mono-, di- and triethanolamines, 2-methyl-2-aminopropanol and derivatives thereof, sodium hydroxide, potassium hydroxide and the compounds of formula (V) below:

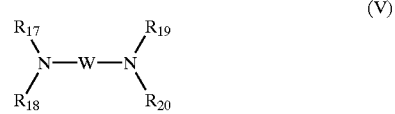

(V)

in which W is a propylene residue optionally substituted with a hydroxyl group or a C$_1$–C$_4$ alkyl radical; R$_{17}$, R$_{18}$, R$_{19}$ and R$_{20}$, which may be identical or different, represent a hydrogen atom or a C$_1$–C$_4$ alkyl or C$_1$–C$_4$ hydroxyalkyl radical.

The ready-to-use dye composition according to the invention can also contain various adjuvants used conventionally in compositions for the dyeing of the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, anti-oxidants, enzymes other than the 2-electron oxido-reductases used in accordance with the invention, such as, for example, peroxidases, penetration agents, sequestering agents, fragrances, buffers, dispersing agents, conditioners such as, for example, silicones which may or may not be volatile or modified, film-forming agents, ceramides, preserving agents and opacifiers. Needless to say, a person skilled in the art will take care to select this or these optional complementary compound(s) such that the advantageous properties intrinsically associated with the ready-to-use dye composition according to the invention are not, or are not substantially, adversely affected by the addition or additions envisaged.

The ready-to-use dye composition in accordance with the invention can exist in various forms, such as in the form of liquids, creams or gels, which may be pressurized, or in any other form suitable for dyeing keratin fibers, and, in particular, human hair. In this case the oxidation dyes and the 2-electron oxidoreductase(s) are present in the same ready-to-use composition, and consequently the composition must be free of gaseous oxygen, so as to avoid any premature oxidation of the oxidation dye(s).

A subject of the invention is also a process for dyeing keratin fibers, and, in particular, human keratin fibers such as the hair, using the ready-to-use dye composition as defined above. According to this process, at least one ready-to-use dye composition as defined above is applied to the fibers, for a period sufficient to develop the desired coloration, after which the fibers are rinsed, optionally washed with shampoo, rinsed again and dried. The time required to develop the coloration on the keratin fibers usually ranges from 3 to 60 minutes, and even more preferably from 5 to 40 minutes.

According to one specific embodiment of the invention, the process includes a preliminary step which comprises separately storing: a composition (A) comprising, in a medium suitable for dyeing, at least one oxidation base and at least one coupler chosen from substituted meta-diphenols, the composition (A) being free from any additional coupler chosen from substituted meta-phenylenediamines and from any polymer chosen from anionic amphiphilic polymers comprising at least one hydrophilic unit and at least one allyl ether unit having a fatty chain; and, a composition (B) comprising, in a medium suitable for dyeing, at least one enzyme of 2-electron oxidoreductase type in the presence of at least one donor for the enzyme, the composition (B) being free from any polymer chosen from anionic amphiphilic polymers comprising at least one hydrophilic unit and at least one allyl ether unit having a fatty chain; and then mixing them together at the time of use, after which this mixture is applied to the keratin fibers.

Another subject of the invention is a multi-compartment dyeing device or "kit" or any other multi-compartment packaging system, a first compartment of which comprises composition (A) as defined above and a second compartment of which comprises composition (B) as defined above. These devices can be equipped with means for delivering the desired mixture onto the hair, such as the devices described in French patent FR-2,586,913, incorporated herein by reference, in the name of L'Oréal.

The present invention is further illustrated by the following examples which are designed to teach those of ordinary skill in the art how to practice the invention. The following examples are merely illustrative of the invention and should not be construed as limiting the invention as claimed.

EXAMPLE 1 OF DYEING

The ready-to-use dye composition below was prepared:

| | |
|---|---|
| para-Phenylenediamine | 0.324 g |
| 2-Methyl-1,3-dihydroxybenzene | 0.372 g |
| Ethanol | 10.0 g |
| Uric acid | 1.0 g |
| Uricase from Arthrobacter globiformis, sold by the company Sigma | 20,000 units (*) |
| 2-Amino-2-methyl-1-propanol, qs pH 9.5 | |
| Demineralized water, qs | 100 g |

(*) NB: One unit corresponds to the amount of enzyme oxidizing one micromol of uric acid per minute at 30° C. and at pH 8.5.

The ready-to-use dye composition described above was applied to locks of natural grey hair containing 90% white hairs, for 30 minutes at 30° C. The hair was then rinsed, washed with a standard shampoo and then dried. The hair was dyed in a brown shade.

The foregoing written description relates to various embodiments of the present invention. Numerous changes and modifications may be made therein without departing from the spirit and scope of the invention as defined in the following claims.

What is claimed is:

1. A ready-to-use composition for oxidation dyeing of keratin fibers comprising:
   at least one oxidation base,
   at least one coupler chosen from substituted meta-diphenols,
   at least one 2-electron oxidoreductase enzyme, and
   at least one donor for said at least one 2-electron oxidoreductase enzyme;
   wherein said composition is free from any additional coupler chosen from substituted meta-phenylenediamines and from any polymer chosen from anionic amphiphilic polymers comprising at least one hydrophilic unit and at least one allyl ether unit having a fatty chain.

2. A composition according to claim 1, wherein said keratin fibers are human keratin fibers.

3. A composition according to claim 2, wherein said human keratin fibers are human hair.

4. A composition according to claim 1, wherein said composition is in a medium suitable for dyeing.

5. A composition according to claim 1, wherein said at least one 2-electron oxidoreductase enzyme is chosen from pyranose oxidases, glucose oxidases, glycerol oxidases, lactate oxidases, pyruvate oxidases and uricases.

6. A composition according to claim 1, wherein said at least one 2-electron oxidoreductase enzyme is chosen from uricases of animal, microbiological or biotechnological origin.

7. A composition according to claim 1, wherein said at least one 2-electron oxidoreductase enzyme is present in an amount ranging from 0.01 to 20% by weight relative to the total weight of the composition.

8. A composition according to claim 7, wherein said at least one 2-electron oxidoreductase enzyme is present in an amount ranging from 0.1 to 5% by weight relative to the total weight of the composition.

9. A composition according to claim 6, wherein said donor for said at lease one 2-electron oxidoreductase enzyme is chosen from uric acid and its salts.

10. A composition according to claim 1, wherein said at least one donor for said at least one 2-electron oxidoreductase enzyme is present in an amount ranging from 0.01 to 20% by weight relative to the total weight of the composition.

11. A composition according to claim 10, wherein said at least one donor for said at least one 2-electron oxidoreductase enzyme is present in an amount ranging from 0.1 to 5% by weight relative to the total weight of the composition.

12. A composition according to claim 1, wherein said at least one oxidation base is chosen from para-phenylenediamines, double bases, para-aminophenols, ortho-aminophenols and heterocyclic bases.

13. A composition according to claim 12, wherein said para-phenylenediamines are chosen from the compounds of formula (I) and the acid addition salts thereof:

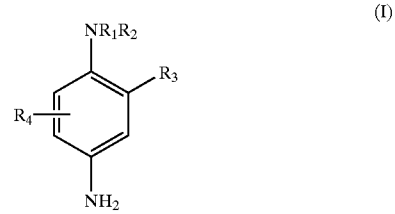

in which:
   $R_1$ is chosen from a hydrogen atom, a $C_1$–$C_4$ alkyl radical, a $C_1$–$C_4$ monohydroxyalkyl radical, a $C_2$–$C_4$ polyhydroxyalkyl radical, a ($C_1$–$C_4$)alkoxy($C_1$–$C_4$)alkyl radical, a $C_1$–$C_4$ alkyl radical substituted with a nitrogenous group, a phenyl radical and a 4'-aminophenyl radical;
   $R_2$ is chosen from a hydrogen atom, a $C_1$–$C_4$ alkyl radical, a $C_1$–$C_4$ monohydroxyalkyl radical, a $C_2$–$C_4$ polyhydroxyalkyl radical, a $(C_1-C_4)$alkoxy$(C_1-C_4)$alkyl radical and a $C_1-C_4$ alkyl radical substituted with a nitrogenous group;

$R_3$ is chosen from a hydrogen atom, a halogen atom, a $C_1-C_4$ alkyl radical, a $C_1-C_4$ monohydroxyalkyl radical, a $C_1-C_4$ hydroxyalkoxy radical, an acetylamino$(C_1-C_4)$alkoxy radical, a $C_1-C_4$ mesylaminoalkoxy radical and a carbamoylamino$(C_1-C_4)$alkoxy radical, $R_4$ is chosen from a hydrogen or halogen atom and a $C_1-C_4$ alkyl radical.

14. A composition according to claim 13, wherein said halogen atom of $R_3$ is chosen from chlorine, bromine, iodine and fluorine atoms.

15. A composition according to claim 13, wherein said para-phenylenediamines of formula (I) are chosen from para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N-(β-methoxyethyl)-para-phenylenediamine, and acid addition salts thereof.

16. A composition according to claim 12 wherein said double bases are chosen from compounds of formula (II), and acid addition salts thereof:

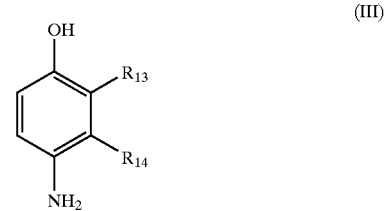

in which:

$Z_1$ and $Z_2$, which are identical or different, are chosen from a hydroxyl radical and an $-NH_2$ radical which are optionally substituted with a $C_1-C_4$ alkyl radical or with a linker arm Y;

said linker arm Y is a linear or branched alkylene chain containing from 1 to 14 carbon atoms, which is optionally interrupted by or terminated with one or more nitrogenous groups, optionally interrupted by or terminated with one or more hetero atoms, and optionally substituted with one or more hydroxyl or $C_1-C_6$ alkoxy radicals;

$R_5$ and $R_6$ are chosen from a hydrogen atom, a halogen atom, a $C_1-C_4$ alkyl radical, a $C_1-C_4$ monohydroxyalkyl radical, a $C_2-C_4$ polyhydroxyalkyl radical, a $C_1-C_4$ aminoalkyl radical and a linker arm Y;

$R_7$, $R_8$, $R_9$, $R_{10}$, $R_{11}$ and $R_{12}$, which are identical or different, are chosen from a hydrogen atom, a linker arm Y and a $C_1-C_4$ alkyl radical;

with the proviso that said compounds of formula (II) contain only one linker arm Y per molecule.

17. A composition according to claim 16, wherein said one or more hetero atoms optionally terminating said linker arm Y are chosen from oxygen, sulphur and nitrogen atoms.

18. A composition according to claim 16, wherein said double bases of formula (II) are chosen from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4'-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and acid addition salts thereof.

19. A composition according to claim 12, wherein said para-aminophenols are chosen from compounds of formula (III), and acid addition salts thereof:

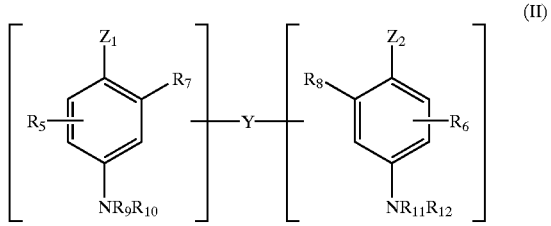

in which:

$R_{13}$ is chosen from a hydrogen atom, a halogen atom, a $C_1-C_4$ alkyl radical, a $C_1-C_4$ monohydroxyalkyl radical, a $(C_1-C_4)$alkoxy$(C_1-C_4)$alkyl radical, a $C_1-C_4$ aminoalkyl radical, and a hydroxy$(C_1-C_4)$alkylamino $(C_1-C_4)$alkyl radical, $R_{14}$ is chosen from a hydrogen atom, a halogen atom, a $C_1-C_4$ alkyl radical, a $C_1-C_4$ monohydroxyalkyl radical, a $C_2-C_4$ polyhydroxyalkyl radical, a $C_1-C_4$ aminoalkyl radical, $C_1-C_4$ cyanoalkyl radical, and a $(C_1-C_4)$ alkoxy-$(C_1-C_4)$ alkyl radical, with the proviso that at least one of $R_{13}$ and $R_{14}$ is a hydrogen atom.

20. A composition according to claim 19, wherein said para-aminophenols of formula (III) are chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and acid addition salts thereof.

21. A composition according to claim 12, wherein said ortho-aminophenols are chosen from 2-aminophenol, 2-amino-5-methylphenol, 2-amino-6-methylphenol and 5-acetamido-2-aminophenol, and acid addition salts thereof.

22. A composition according to claim 12, wherein said heterocyclic bases are chosen from pyridine derivatives, pyrimidine derivatives and pyrazole derivatives, and acid addition salts thereof.

23. A composition according to claim 1, wherein said at least one oxidation base is present in an amount ranging from 0.0005 to 12% by weight relative to the total weight of the composition.

24. A composition according to claim 23, wherein said at least one oxidation base is present in an amount ranging from 0.005 to 8% by weight relative to the total weight of the composition.

25. A composition according to claim 1, wherein said substituted meta-diphenols are chosen from compounds of formula (IV), and acid addition salts thereof:

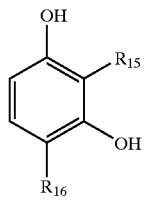

(IV)

in which:
$R_{15}$ and $R_{16}$, which are identical or different, are chosen from a hydrogen atom, a $C_1$–$C_4$ alkyl radical and a halogen atom chosen from chlorine, bromine and fluorine;
with the proviso that at least one of $R_{15}$ and $R_{16}$ is not a hydrogen atom.

26. A composition according to claim 25, wherein said meta-diphenols of formula (IV) are chosen from 2-methyl-1,3-dihydroxybenzene, 4-chloro-1,3-dihydroxybenzene and 2-chloro-1,3-dihydroxybenzene, and acid addition salts thereof.

27. A composition according to claim 26, wherein said meta-diphenols of formula (IV) are chosen from 2-methyl-1,3-dihydroxybenzene, acid addition salts thereof and mixtures thereof.

28. A composition according to claim 1, wherein said substituted meta-diphenols are present in an amount ranging from 0.0001 to 8% by weight relative to the total weight of the composition.

29. A composition according to claim 28, wherein said substituted meta-diphenols are present in an amount ranging from 0.005 to 5% by weight relative to the total weight of the composition.

30. A composition according to claim 25, wherein said acid addition salts are chosen from hydrochlorides, hydrobromides, sulphates, tartrates, lactates and acetates.

31. A composition according to claim 22, wherein said acid addition salts are chosen from hydrochlorides, hydrobromides, sulphates, tartrates, lactates and acetates.

32. A composition according to claim 21, wherein said acid addition salts are chosen from hydrochlorides, hydrobromides, sulphates, tartrates, lactates and acetates.

33. A composition according to claim 19, wherein said acid addition salts are chosen from hydrochlorides, hydrobromides, sulphates, tartrates, lactates and acetates.

34. A composition according to claim 16, wherein said acid addition salts are chosen from hydrochlorides, hydrobromides, sulphates, tartrates, lactates and acetates.

35. A composition according to claim 13, wherein said acid addition salts are chosen from hydrochlorides, hydrobromides, sulphates, tartrates, lactates and acetates.

36. A composition according to claim 1, further comprising at least one additional coupler, at least one direct dye, or both at least one additional coupler and at least one direct dye.

37. A composition according to claim 1, wherein said composition has a pH ranging from 5 to 11.

38. A composition according to claim 1, wherein said composition comprises at least one peroxidase.

39. A method for dyeing keratin fibers, comprising applying at least one ready-to-use dye composition to said fibers and developing for a period sufficient to achieve the desired coloration, wherein said at least one ready-to-use dye composition comprises:
at least one oxidation base,
at least one coupler chosen from substituted meta-diphenols,
at least one 2-electron oxidoreductase enzyme, and
at least one donor for said at least one 2-electron oxidoreductase enzyme;
wherein said composition is free from any additional coupler chosen from substituted meta-phenylenediamines and from any polymer chosen from anionic amphiphilic polymers comprising at least one hydrophilic unit and at least one allyl ether unit having a fatty chain.

40. A method according to claim 39, wherein said keratin fibers are human keratin fibers.

41. A method according to claim 40, wherein said human keratin fibers are human hair.

42. A method for dyeing keratin fibers, comprising:
separately storing a first composition,
separately storing a second composition,
thereafter mixing said first and second compositions,
applying said mixture to said fibers, and
developing for a period sufficient to achieve the desired coloration,
wherein said first composition comprises at least one oxidation base and at least one coupler chosen from substituted meta-diphenols, said first composition being free from any additional coupler chosen from substituted meta-phenylenediamines and from any polymer chosen from anionic amphiphilic polymers comprising at least one hydrophilic unit and at least one allyl ether unit having a fatty chain, and
wherein said second composition comprises at least one 2-electron oxidoreductase enzyme in the presence of at least one donor for said enzyme, said second composition being free from any polymer chosen from anionic amphiphilic polymers comprising at least one hydrophilic unit and at least one allyl ether unit having a fatty chain.

43. A multi-compartment dyeing kit comprising at least two separate compartments, wherein a first compartment contains a first composition and a second compartment contains a second composition,
wherein said first composition comprises at least one oxidation base and at least one coupler chosen from substituted meta-diphenols, said first composition being free from any additional coupler chosen from substituted meta-phenylenediamines and from any polymer chosen from anionic amphiphilic polymers comprising at least one hydrophilic unit and at least one allyl ether unit having a fatty chain; and
wherein said second composition comprises at least one 2-electron oxidoreductase enzyme in the presence of at least one donor for said enzyme, said second composition being free from any polymer chosen from anionic amphiphilic polymers comprising at least one hydrophilic unit and at least one allyl ether unit having a fatty chain.

* * * * *

UNITED STATES PATENT AND TRADEMARK OFFICE
CERTIFICATE OF CORRECTION

PATENT NO. : 6,419,710 B1  
DATED : July 16, 2002  
INVENTOR(S) : Demeulenaere et al.

It is certified that error appears in the above-identified patent and that said Letters Patent is hereby corrected as shown below:

Column 10,  
Line 30, "lease" should read -- least --.

Column 12,  
Line 46, before "$C_1$-$C_4$" insert -- a --.

Signed and Sealed this

Thirty-first Day of December, 2002

JAMES E. ROGAN  
*Director of the United States Patent and Trademark Office*